United States Patent
Thompson

(10) Patent No.: US 9,364,302 B2
(45) Date of Patent: Jun. 14, 2016

(54) PROCESS AND SYSTEMS FOR MOLDING THERMOSETTING PLASTICS

(75) Inventor: Timothy C. Thompson, Fountain Hills, AZ (US)

(73) Assignee: GLOBAL DENTAL SCIENCE LLC, Scottsdale, AZ (US)

( * ) Notice: Subject to any disclaimer, the term of this patent is extended or adjusted under 35 U.S.C. 154(b) by 655 days.

(21) Appl. No.: 13/369,238

(22) Filed: Feb. 8, 2012

(65) Prior Publication Data

US 2013/0249132 A1 Sep. 26, 2013

(51) Int. Cl.
| | |
|---|---|
| *B29C 43/10* | (2006.01) |
| *A61C 13/20* | (2006.01) |
| *B29C 43/00* | (2006.01) |
| B29K 33/00 | (2006.01) |
| B29K 101/10 | (2006.01) |

(52) U.S. Cl.
CPC ............... *A61C 13/20* (2013.01); *B29C 43/003* (2013.01); *B29C 43/10* (2013.01); *B29K 2033/08* (2013.01); *B29K 2101/10* (2013.01)

(58) Field of Classification Search
CPC .. B29C 35/002; B29C 35/02; B29C 35/0288; B29C 43/10; B29K 2033/08; B30B 11/001; B30B 11/002
USPC .................... 264/40.6, 40.1, 319, 330, 331.4, 264/311.15, 311.18, 40.3, 570
See application file for complete search history.

(56) References Cited

U.S. PATENT DOCUMENTS

| | | | |
|---|---|---|---|
| 200,445 A | 2/1878 | Fahnestock | |
| 321,847 A | 7/1885 | Peirce et al. | |
| 711,324 A | 10/1902 | Lacy | |
| 1,223,450 A | 4/1917 | Van Allen | |
| 1,293,627 A | 2/1919 | Bowers | |
| 1,585,348 A | 5/1926 | Hick et al. | |
| 1,652,910 A | 12/1927 | Psayla | |
| 1,714,185 A | 5/1929 | Hugh | |
| 1,863,591 A | 6/1932 | Crowell | |
| 1,914,606 A | 6/1933 | Kinna et al. | |
| 2,107,181 A | 2/1938 | Guyton | |
| 2,418,833 A | 4/1947 | Harris et al. | |

(Continued)

FOREIGN PATENT DOCUMENTS

| | | |
|---|---|---|
| CA | 2505892 | 5/2004 |
| JP | 2008307281 | 12/2008 |

(Continued)

OTHER PUBLICATIONS

USPTO; Final Office Action dated Mar. 6, 2014 in U.S. Appl. No. 13/249,210.

(Continued)

*Primary Examiner* — Christina Johnson
*Assistant Examiner* — Xue Liu
(74) *Attorney, Agent, or Firm* — Harvey Law; Derrick W. Harvey

(57) ABSTRACT

Process and systems for molding or forming products from thermosetting plastics. The system utilizes a deformable container that is placed within the cavity of the housing of the mold with the resins and initiator mixed therein. As a piston slides into the cavity, the upper edges of the container engage between the housing and the piston to seal the housing form leakage. The pressure of the piston along with heat on the housing enable the curing process to be controlled to minimize shrinkage and porosity.

17 Claims, 4 Drawing Sheets

(56) References Cited

U.S. PATENT DOCUMENTS

| | | | |
|---|---|---|---|
| 2,472,492 | A | 6/1949 | Saffir |
| 2,641,835 | A | 6/1953 | Greenmun |
| 2,985,961 | A | 5/1961 | Schwartz |
| 2,994,957 | A | 8/1961 | Mcleod |
| 3,083,459 | A | 4/1963 | McMurry et al. |
| 3,241,238 | A | 3/1966 | Kertsten |
| 3,644,996 | A | 2/1972 | Weinkle |
| 3,667,123 | A | 6/1972 | Huey |
| 3,727,309 | A | 4/1973 | Huey |
| 3,748,739 | A | 7/1973 | Thibert |
| 3,813,777 | A | 6/1974 | Van Handel et al. |
| 3,844,702 | A * | 10/1974 | Dimmer et al. ............... 425/425 |
| 4,029,632 | A | 6/1977 | Gross et al. |
| 4,227,877 | A | 10/1980 | Tureaud et al. |
| 4,247,287 | A | 1/1981 | Gigante |
| 4,299,573 | A | 11/1981 | Ricci |
| 4,533,325 | A | 8/1985 | Blair |
| 4,591,341 | A | 5/1986 | Andrews |
| 4,634,377 | A | 1/1987 | Behrend |
| 4,784,608 | A | 11/1988 | Mays |
| 4,931,016 | A | 6/1990 | Sillard |
| 5,098,296 | A | 3/1992 | Cullen |
| 5,151,044 | A | 9/1992 | Rotsaert |
| 5,188,529 | A | 2/1993 | Luth |
| 5,427,906 | A | 6/1995 | Hansen |
| 5,672,305 | A | 9/1997 | Kogure |
| 5,711,668 | A | 1/1998 | Huestis |
| 5,716,214 | A | 2/1998 | Lund |
| 5,718,584 | A | 2/1998 | Wong |
| 5,833,461 | A | 11/1998 | Wong |
| 5,839,900 | A | 11/1998 | Billet et al. |
| 6,056,547 | A | 5/2000 | Names |
| 6,139,322 | A | 10/2000 | Liu |
| 6,149,427 | A | 11/2000 | Van Handel |
| 6,224,372 | B1 | 5/2001 | Ibsen et al. |
| 6,227,851 | B1 | 5/2001 | Chishti |
| 6,384,107 | B2 | 5/2002 | Liu |
| 6,422,864 | B1 | 7/2002 | Glatt |
| 6,488,503 | B1 | 12/2002 | Lichkus et al. |
| 6,616,444 | B2 | 9/2003 | Andreiko et al. |
| 6,851,949 | B1 | 2/2005 | Sachdeva |
| 7,021,934 | B2 | 4/2006 | Aravena |
| 7,153,135 | B1 | 12/2006 | Thomas |
| 7,234,940 | B2 | 6/2007 | Weissman |
| 7,433,810 | B2 | 10/2008 | Pavloskaia et al. |
| 7,474,932 | B2 | 1/2009 | Geng |
| 7,758,345 | B1 | 7/2010 | Christensen |
| 8,043,091 | B2 | 10/2011 | Schmitt |
| 8,348,669 | B1 | 1/2013 | Schmitt |
| 8,567,408 | B2 | 10/2013 | Roettger |
| 8,641,938 | B2 | 2/2014 | Howe |
| 8,801,431 | B2 | 8/2014 | Thompson et al. |
| 8,875,398 | B2 | 11/2014 | Balshi et al. |
| 9,055,993 | B2 | 6/2015 | Grobbee et al. |
| 2002/0015934 | A1 | 2/2002 | Rubbert et al. |
| 2002/0180760 | A1 | 12/2002 | Rubbert et al. |
| 2003/0108845 | A1 | 6/2003 | Giovannone |
| 2003/0162147 | A1 | 8/2003 | Dequeker |
| 2003/0163291 | A1 | 8/2003 | Jordan et al. |
| 2003/0211444 | A1 | 11/2003 | Andrews |
| 2004/0005530 | A1 | 1/2004 | Mullaly |
| 2004/0029068 | A1 | 2/2004 | Sachdeva et al. |
| 2004/0219490 | A1 | 11/2004 | Gartner et al. |
| 2005/0175957 | A1 | 8/2005 | Haje |
| 2005/0186539 | A1 | 8/2005 | McLean et al. |
| 2005/0284489 | A1 | 12/2005 | Ambis |
| 2006/0040232 | A1 | 2/2006 | Shoup |
| 2006/0040236 | A1 | 2/2006 | Schmitt |
| 2006/0063135 | A1 | 3/2006 | Mehl |
| 2006/0210945 | A1 | 9/2006 | Savic et al. |
| 2006/0286507 | A1 | 12/2006 | Dequeker |
| 2007/0154868 | A1 | 7/2007 | Scharlack et al. |
| 2007/0231774 | A1 | 10/2007 | Massad |
| 2008/0085489 | A1 | 4/2008 | Schmitt |
| 2008/0090207 | A1 | 4/2008 | Rubbert |
| 2008/0127698 | A1 | 6/2008 | Luckey et al. |
| 2008/0206710 | A1 | 8/2008 | Kruth et al. |
| 2008/0206714 | A1 | 8/2008 | Schmitt |
| 2008/0209974 | A1 | 9/2008 | Ewolski et al. |
| 2008/0300716 | A1 | 12/2008 | Kopelman |
| 2009/0148813 | A1 | 6/2009 | Sun et al. |
| 2009/0162813 | A1 | 6/2009 | Glor |
| 2009/0243162 | A1 * | 10/2009 | Shepard ................. A61C 13/14 264/570 |
| 2009/0287332 | A1 | 11/2009 | Adusumilli et al. |
| 2009/0291407 | A1 | 11/2009 | Kuo |
| 2009/0325125 | A1 | 12/2009 | Diangelo et al. |
| 2010/0015572 | A1 | 1/2010 | Dirkes et al. |
| 2010/0062394 | A1 | 3/2010 | Jones et al. |
| 2010/0086186 | A1 | 4/2010 | Zug et al. |
| 2010/0094446 | A1 | 4/2010 | Baloch et al. |
| 2010/0105011 | A1 | 4/2010 | Karkar et al. |
| 2010/0324875 | A1 | 12/2010 | Kalili |
| 2011/0045442 | A1 | 2/2011 | Adusumilli |
| 2011/0112804 | A1 | 5/2011 | Chishti et al. |
| 2011/0129796 | A1 | 6/2011 | Riggio |
| 2011/0236856 | A1 | 9/2011 | Kanazawa et al. |
| 2011/0244417 | A1 | 10/2011 | Hilsen et al. |
| 2012/0058449 | A1 | 3/2012 | Sklarski et al. |
| 2012/0095732 | A1 | 4/2012 | Fisker et al. |
| 2012/0100500 | A1 | 4/2012 | Gao |
| 2012/0178045 | A1 | 7/2012 | Massad |
| 2012/0179281 | A1 | 7/2012 | Steingart et al. |
| 2012/0258426 | A1 | 10/2012 | Boe |
| 2012/0285019 | A1 | 11/2012 | Schechner et al. |
| 2012/0329008 | A1 | 12/2012 | Fishman et al. |
| 2013/0108988 | A1 | 5/2013 | Simoncic |
| 2013/0209962 | A1 | 8/2013 | Thompson et al. |
| 2013/0216978 | A1 | 8/2013 | Thompson et al. |
| 2013/0218532 | A1 | 8/2013 | Thompson et al. |
| 2013/0221554 | A1 | 8/2013 | Jung et al. |
| 2013/0280672 | A1 | 10/2013 | Thompson et al. |
| 2013/0316302 | A1 | 11/2013 | Fisker |
| 2014/0045967 | A1 | 2/2014 | Thomas et al. |
| 2014/0272796 | A1 | 9/2014 | Grobbee et al. |
| 2015/0010885 | A1 | 1/2015 | Balshi et al. |
| 2015/0037760 | A1 | 2/2015 | Thompson et al. |
| 2015/0064653 | A1 | 3/2015 | Grobbee et al. |
| 2015/0134094 | A1 | 5/2015 | Thompson et al. |
| 2015/0230891 | A1 | 8/2015 | Grobbee et al. |
| 2015/0245891 | A1 | 9/2015 | Grobbee |
| 2015/0245892 | A1 | 9/2015 | Grobbee |

FOREIGN PATENT DOCUMENTS

| | | |
|---|---|---|
| WO | 0132096 | 12/2001 |
| WO | 2009105661 | 8/2009 |
| WO | 2009105700 | 8/2009 |
| WO | 2010022479 | 3/2010 |
| WO | 2012041329 | 4/2012 |
| WO | 2012061652 | 5/2012 |
| WO | 2012061655 | 5/2012 |
| WO | 2012061659 | 5/2012 |
| WO | 2012061660 | 5/2012 |
| WO | 2014130536 | 8/2014 |
| WO | 2015031062 | 3/2015 |

OTHER PUBLICATIONS

USPTO; Restriction Requirement dated Dec. 23, 2013 in U.S. Appl. No. 13/823,466.
EPO; European Search Report dated Mar. 4, 2014 in Application No. 11838839.6.
PCT; International Search Report and Written Opinion dated Jul. 18, 2012 in Application No. PCT/US2011/059230.
PCT; International Preliminary Report on Patentability dated May 8, 2013 in Application No. PCT/US2011/059230.
PCT; International Search Report and Written Opinion dated Jul. 18, 2012 in Application No. PCT/US2011/059235.
PCT; International Preliminary Report on Patentability dated May 8, 2013 in Application No. PCT/US2011/059235.
PCT; International Search Report and Written Opinion dated Jul. 9, 2012 in Application No. PCT/US2011/059239.

(56) References Cited

OTHER PUBLICATIONS

PCT; International Preliminary Report on Patentability dated May 8, 2013 in Application No. PCT/US2011/059239.
PCT; International Search Report and Written Opinion dated Jul. 18, 2012 in Application No. PCT/US2011/059240.
PCT; International Preliminary Report on Patentability dated May 8, 2013 in Application No. PCT/US2011/059240.
USPTO; Restriction Requirement dated Sep. 5, 2014 in U.S. Appl. No. 13/823,621.
USPTO; Office Action dated Aug. 21, 2014 in U.S. Appl. No. 14/195,348.
USPTO; Final Office Action dated Oct. 21, 2014 in U.S. Appl. No. 14/195,348.
PCT; International Search Report and Written Opinion dated Aug. 7, 2014 in Application No. PCT/US2014/023654.
USPTO; Notice of Allowance dated Jun. 6, 2014 in U.S. Appl. No. 13/249,210.
USPTO; Non-Final Office Action dated Jun. 6, 2014 in U.S. Appl. No. 13/823,466.
USPTO; Non-Final Office Action dated Jun. 20, 2014 in U.S. Appl. No. 13/830,963.
USPTO; Restriction Requirement dated Jul. 2, 2014 in U.S. Appl. No. 14/195,348.
EPO; European Search Report and Opinion dated Mar. 3, 2014 in Application No. 11838843.8.
PCT; International Search Report and Written Opinion dated Jul. 25, 2014 in Application No. PCT/US2014/017136.
USPTO; Office Action dated Jan. 5, 2015 in U.S. Appl. No. 12/939,136.
USPTO; Advisory Action dated Feb. 23, 2015 in U.S. Appl. No. 13/830,963.
USPTO; Non-Final Office Action dated Dec. 19, 2014 in U.S. Appl. No. 14/013,295.
USPTO; Office Action dated Sep. 24, 2013 in U.S. Appl. No. 13/249,210.
USPTO; Non-Final Office Action dated Oct. 23, 2014 in U.S. Appl. No. 13/823,621.
USPTO; Final Office Action dated dated Nov. 7, 2014 in U.S. Appl. No. 13/830,963.
USPTO; Non-Final Office Action dated Apr. 9, 2015 in U.S. Appl. No. 12/939,138.
USPTO; Final Office Action dated Mar. 26, 2015 in U.S. Appl. No. 13/823,466.
USPTO; Notice of Allowance dated Jun. 22, 2015 in U.S. Appl. No. 13/823,621.
USPTO; Notice of Allowance dated Apr. 13, 2015 in U.S. Appl. No. 14/013,295.
USPTO; Final Office Action dated Sep. 25, 2015 in U.S. Appl. No. 12/939,136.
USPTO; Final Office Action dated Aug. 19, 2015 in U.S. Appl. No. 12/939,138.
USPTO; Notice of Allowance dated Aug. 24, 2015 in U.S. Appl. No. 13/823,662.
USPTO; Non-Final Office Action dated Aug. 13, 2015 in U.S. Appl. No. 13/830,963.
USPTO; Non-Final Office Action dated Aug. 11, 2015 in U.S. Appl. No. 14/195,348.

* cited by examiner

PROCESS AND SYSTEMS FOR MOLDING THERMOSETTING PLASTICS

FIELD OF THE INVENTION

This invention relates to the field of molding thermosetting plastics, and particularly to the field of molding acrylic.

BACKGROUND OF THE INVENTION

Many products have been created from the use of molding thermosetting plastics. This process typically requires the mixing of monomer resins with a polymerization initiator in a chemical process to create a polymer. This process has more recently been utilized as part of a process to create such products as dentures.

Dentures have been manufactured for centuries to replace all or part of an individuals dentition. More recently, dentures have been manufactured by molding the denture from casts made of the patient's existing dentition. The manufacturing process begins with a preliminary impression of the patient's mouth, which is usually done in wax. This impression is used to prepare a diagnostic cast. While making the impression, the dentist applies pressure to the soft tissues to simulate biting force and extends the borders of the mold to adjacent toothless areas to allow the dentures to better adapt to the gums. A final cast is then formed from the diagnostic cast from gypsum. The final mold is filled acrylic resin to form the denture. The appropriate resin compound are then mixed in liquid form and packed into the mold. A vertical vise may be used to pack the resin compound. Alternatively the liquid acrylic compounds may be poured into the mold. The mold is then heated to initiate the chemical reaction to harden or cure the compound. Once the compound has cured, the mold is broken apart and the denture is removed. The denture is then fitted to the patient with minor revisions.

This process is time consuming and costly. Further, a number of problems may occur during the molding process, particularly with acrylic. These include shrinkage and porosity issues.

SUMMARY OF THE INVENTION

The present invention provides systems and processes for creating products from thermosetting plastics. The preferred embodiment allows molding of the thermosetting plastics while minimizing shrinkage and porosity during the curing process. The preferred embodiment also prevents leakage of the thermosetting plastic during the curing process as well. The preferred embodiment also minimizes clean up of the housing of the mold as well.

One preferred embodiment of the present invention provides a container for mixing the resins and initiator and for holding the mixed resins and initiator during the curing process. The upper edges of the container also provides a sealing mechanism in the mold housing to prevent leakage of the curing components.

The system of one preferred embodiment includes a housing having an inner cavity, a base attached to the housing and a piston slidable in the cavity. A container for mixing and holding the resins and initiator is placed in the cavity so that when the piston slides down to apply pressure against the mixed components, the upper edges of the container engage between the piston and housing to prevent leakage of the mixed components. Force applied against the piston creates pressure against the mixed components while heat is applied to the housing to initiate and control the curing process. The container may be deformable so that impressions may be formed in the final cured product.

The process for creating products from thermostatic plastics includes mixing the resins and initiator in a container, then placing the container in the cavity of a housing. Force is applied to a piston which slides into the cavity against the container. The upper edges of the container engage in the spacing between the piston and housing to seal the housing from leakage of the mixed components. The pressure from the piston and heat applied to the housing provide control of the curing process. Once the plastic has cured, the container can be removed from the housing and then removed from the cured product and discarded.

In a preferred embodiment of the present invention, the thermosetting plastic uses acrylic resins. An appropriate initiator can be selected to control the curing process.

In a preferred embodiment, the process and systems of the present invention are used to create a manufacturing blank. This blank is then used to fabricate a product, such as denture through CAD/CAM or other fabrication processes.

These and other features of the present invention will be evident from the ensuing detailed description of preferred embodiments, from the claims and from the drawings.

DETAILED DESCRIPTION OF PREFERRED EMBODIMENTS

Figure 1:
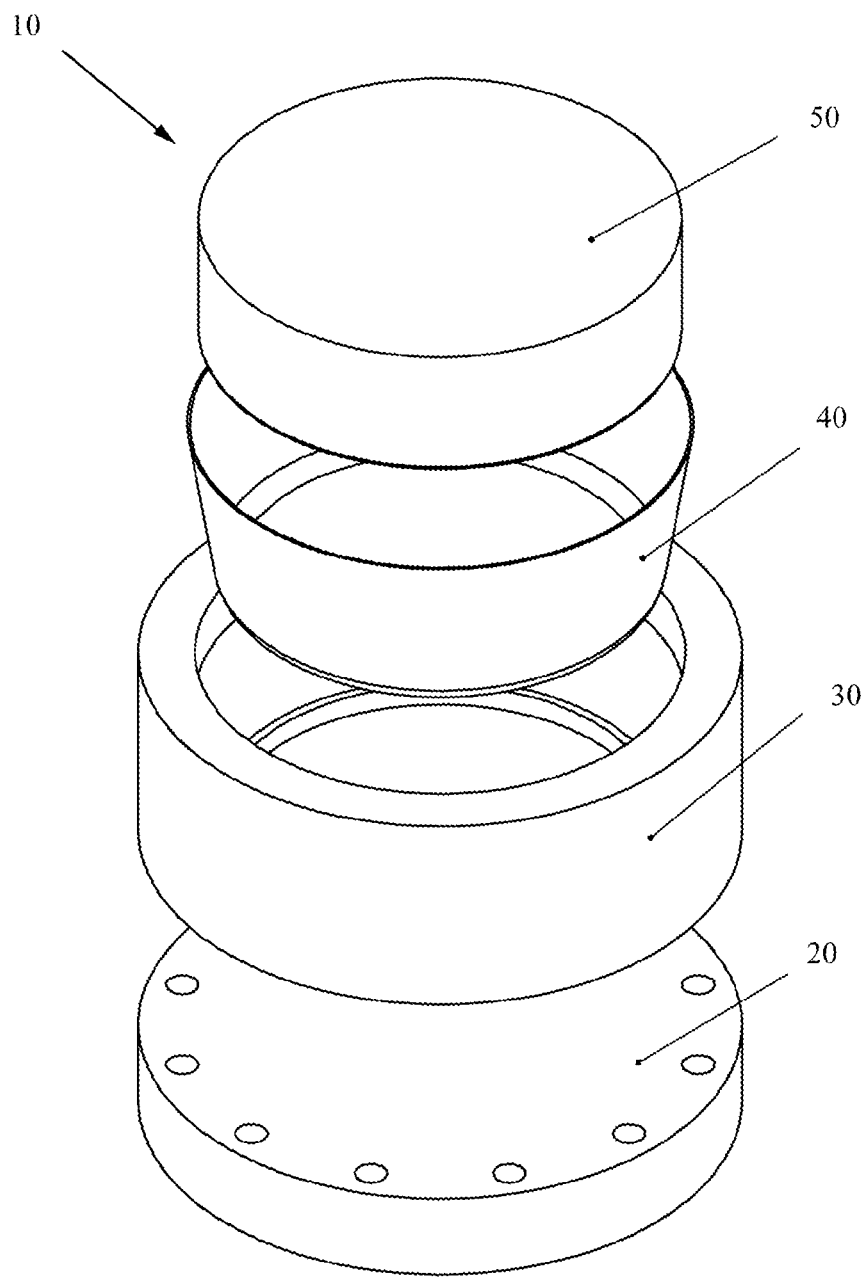
FIG. 1 is an exploded view of the system of a preferred embodiment of the present invention.
Figure 2:
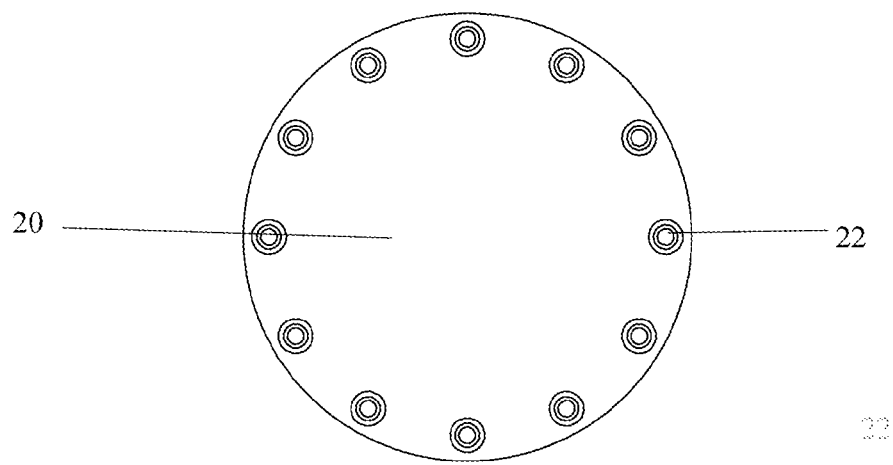
FIG. 2 is a bottom view of the system of FIG. 1.
Figure 3:
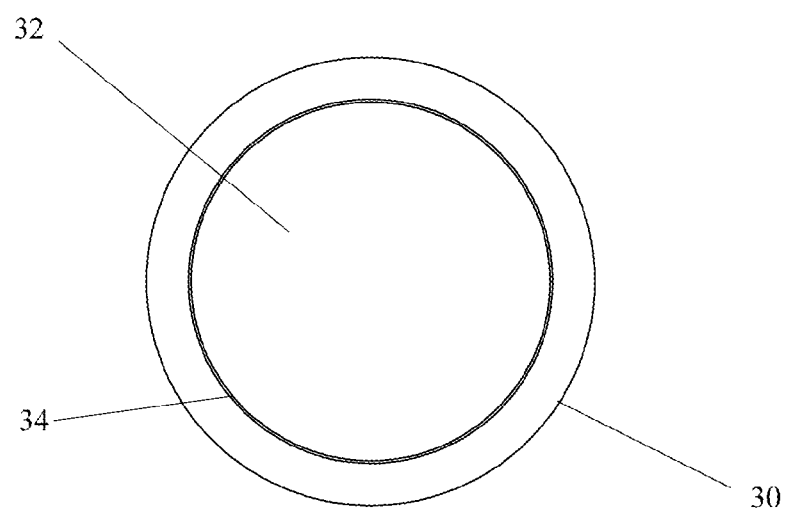
FIG. 3 is a top view of the system of FIG. 1.
Figure 4:
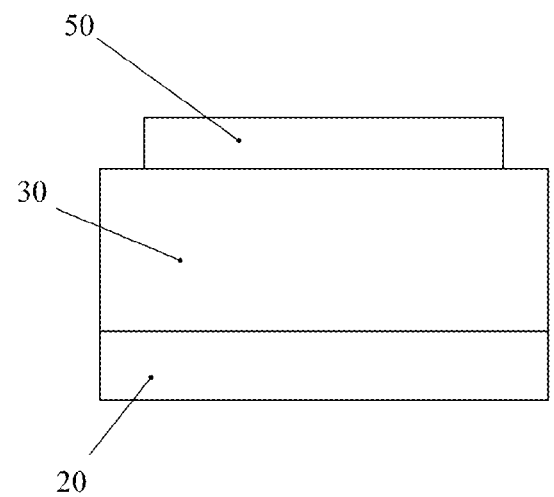
FIG. 4 is a view of the assembled system of FIG. 1.

The present invention provides systems and methods for manufacturing dentures, and more particularly, to the fabrication of the blank for the denture. It is to be expressly understood that this exemplary embodiment is provided for descriptive purposes only and is not meant to unduly limit the scope of the present inventive concept. Other embodiments and variations of the molding process and systems of the present invention are considered within the present inventive concept as set forth in the claims herein. Also, the present invention is primarily discussed for use with dentures for descriptive purposes only and is not meant to be limited solely to this use. It is to be expressly understood that other objects could be fabricated within the present invention as set forth in the claims.

Certain plastics are preferred for particular characteristics. An example of one such material is acrylic. Acrylic is a general term used for any one of the plastics generated through chemical reaction by applying a polymerization initiator and heat to a monomer resin. The monomer resin polyermizes to harden into a solid polymer material. These thermosetting plastics are formed from resins derived from acrylic acid, methacrylic acid or other related compounds. The chemical name for the resin produced from the methyl methacrylate monomer (MMA) is polymethyl methacrylate (PMMA). This particular material is highly durable, resistant to environmental factors and does not easily discolor.

The PMMA resin is mixed with a catalyst, hardener or initiator (collectively referred to as catalyst or initiator) to harden the plastic into a desired shape. The resin and catalyst are mixed together to form a liquid which can then be poured into a mold. The hardening or curing process begins once the two components, resin and catalyst, are mixed together to create a chemical process to form a hard polymer. Two important factors occur during the curing process that affect the final product. These factors are shrinkage of the combined components and heat.

While heat is necessary to initiate the curing process, the exothermic chemical process of curing also generates considerable heat. The exothermic process occurs from the center outward causing considerable temperature gradients and internal stresses. This generated heat can cause bubbles to form in the acrylic creating air porosity in the material. Additional air bubbles may occur due to the initial mixing of the two components and from pouring the liquid into the mold.

An additional problem with casting acrylics into molds is the shrinkage that occurs during the curing process. This shrinkage can range from eight percent to twenty one percent, thus is a significant factor in precisely forming an object from casting acrylic.

These factors are addressed by a number of techniques. These techniques include careful selection of the catalysts to control the exothermic process, utilization of vacuum chambers to remove air, multiple stages of heat application to control the heat of the curing process, and other techniques. One preferred technique is to apply pressure during the curing process. The use of high pressure on the resin and catalyst during the curing process will decrease the cooking of the acrylic during curing, decrease any thermal expansion during the curing, minimize any polymerization shrinkage, decrease the porosity of the acrylic by increasing the evaporation of the polymer and compressing air bubbles created during mixing. The pressure also compensates for the shrinkage factor.

System for Molding or Casting Acrylic

A preferred embodiment of a system for molding acrylic is illustrated in FIGS. 1-4. The system 10 includes a base 20 with housing 30 mounted thereon. Piston 50 slides within housing 30. A driving force, such as a mechanical force, hydraulic, pneumatic or other force application device (not shown) drives the piston 50 through the housing to create pressure within the housing. Cup 40 is mounted within the housing 30 to form a seal between the housing and piston.

The bottom 32 of the housing 30 is mounted to the base 20 by a series of spaced bolts securing the housing to the base as shown in FIGS. 2, 3, 4 and 5 to form a sealed container. The housing 30 is cylindrical with inner opening 32 forming a space for the cup 40, the combined resin and catalyst and the piston 50. A heating element (not shown) applies heat to the housing 30 to initiate the curing process. Temperature and pressure gauges may also be utilized in housing 30 along with ventilation openings to assist in controlling the curing process.

Figure 5:
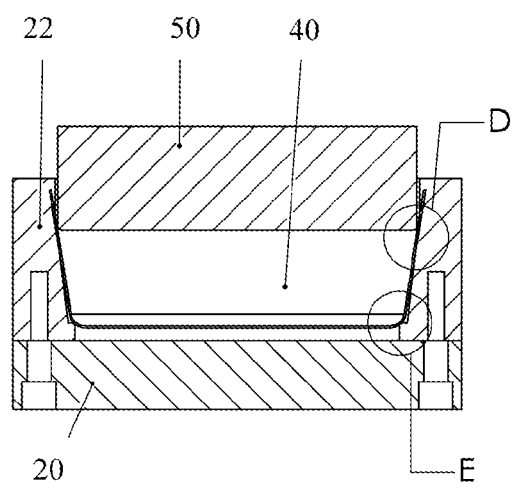
FIG. 5 is a cutaway view of the system of FIG. 1.
Figure 6:
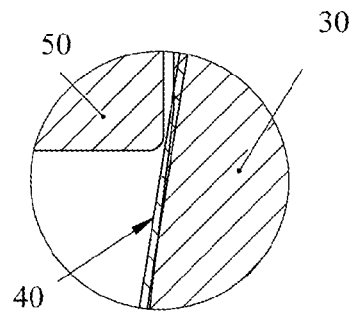
FIG. 6 is a detail view showing the area D of FIG. 5.

The resin and catalyst are mixed in cup 40 which is then placed within housing 30. Force is applied to piston 50 to apply pressure on the combined resin and catalyst. As shown in FIG. 5, the upper edges 42 of the cup 40 engage in the spacing between the housing 30 and piston 50 to form a seal to prevent leakage of the material. This is shown in greater detail in FIG. 6.

Figure 7:
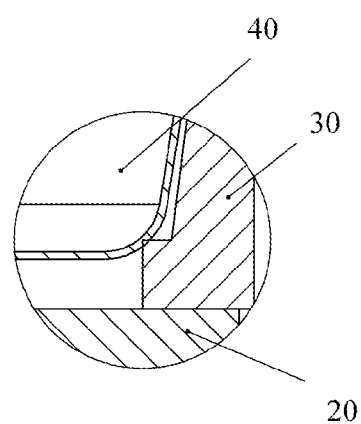
FIG. 7 is a detail view showing the area E of FIG. 5.

The cup 40 can also be used to create special impressions in the shape of the cured acrylic. For example, as shown in FIG. 7, the cup deforms under the pressure from the piston 50 to form a groove in the corner of the final product. Other impressions may be created as well as desired by the interaction of the cup and the housing.

The cup may be formed of plastic or other materials to be deformable under pressie or can be formed of more rigid materials to create a precise shape. The cup 40 also serves other purposes for the molding/casting process. The resin and catalyst can be carefully mixed in the cup which allows the cup to then be inserted into the housing. The cup also protects the housing 30 and base 20 from cured acrylic to minimize later clean-up.

Process of Molding Acrylic

The resins and catalysts are mixed together in the cup 40 to innate the curing process. The cup containing the combined components is then placed in the bottom of housing 40. Force is applied to piston 50 to apply pressure against the cup and combined components along with heat through the housing 30. The combined heat and pressure controls the curing process. The edges of the cup 40 engage between the piston 50 and the housing 40 to seal the housing to prevent leakage of the acrylic material. Once the acrylic has cured, the piston is retracted and the cured acrylic product is removed. The cup allows easy release of the product from the housing. The cup can then be removed from the cured product and discarded.

Applications

One application of the preferred embodiment of the present invention is to create precise blanks for manufacturing dentures. Blanks are formed using the above described system in the steps of the above described process to create manufacturing pucks. These pucks are then fabricated into dentures using CAD/CAM or other machining processes.

It is to be expressly understood that the above described embodiments are intended for explanatory purposes only and are not meant to limit the scope of the claimed inventions.

What is claimed is:

1. A method for molding a thermosetting plastic comprising:
   providing monomer resins;
   providing a polymerization initiator;
   mixing the resins and the initiator together;
   providing a container for holding the mixed resins and initiator, wherein said container is formed of deformable material to create impressions in the cured thermosetting plastic;
   placing the container in a housing cavity;
   applying heat to the housing cavity;
   applying pressure against the mixed resins and initiator;
   controlling a curing process by controlling the heat and pressure to minimize porosity and shrinkage of the thermosetting plastic;
   removing the container with the cured plastic from the housing; and
   forming a blank for manufacturing dentures from said method.

2. The method of claim 1, wherein the step of mixing resins and initiator comprises:
   mixing said resins and initiator in said container.

3. The method of claim 1, wherein container comprises:
   a plastic cup.

4. The method of claim 1, wherein the step of placing the container in the housing cavity comprises:
   forming a seal with the upper edges of the container in the housing to prevent leakage as pressure is applied against the thermosetting plastic.

5. A method for molding a thermosetting plastic comprising:
   providing monomer resins;
   providing a polymerization initiator;
   mixing the resins and the initiator together;
   providing a container for holding the mixed resins and initiator;
   placing the container in a housing cavity;

applying heat to the housing cavity;
applying pressure against the mixed resins and initiator, wherein the step of applying pressure against the mixed resins and initiator comprises:
  providing a piston sliding in the housing against the mixed resins and initiator; and
  providing upper edges of the container to engage in the space between the piston and the housing to form a seal from leakage of the resins and initiator;
controlling a curing process by controlling the heat and pressure to minimize porosity and shrinkage of the thermosetting plastic;
removing the container with the cured plastic from the housing; and
forming a blank for manufacturing dentures from said method.

6. The method of claim 1, wherein the resins comprise: acrylic resins.

7. A method for molding a thermosetting plastic comprising:
  placing a container containing mixed resin and initiator in a housing cavity;
  providing a piston sliding in the housing cavity against the mixed resin and initiator;
  providing upper edges of the container to engage in a space between the piston and the housing to form a seal from leakage of the mixed resin and the initiator;
  applying heat to the housing cavity;
  applying pressure against the mixed resin and initiator by the piston;
  controlling a curing process of the resin and initiator into a cured thermosetting plastic by controlling at least one of the heat and the pressure to minimize at least one of: porosity and shrinkage of the mixed resin and initiator; and
  removing the cured thermosetting plastic from the housing.

8. The method according to claim 7, further comprising:
  mixing a monomer resin and a polymerization initiator to form the mixed resin and initiator,
  wherein the monomer resin and the polymerization initiator are mixed in the container.

9. The method according to claim 7, wherein the mixed resin and initiator comprises a monomer resin and a polymerization initiator.

10. The method according to claim 9, wherein the monomer resin comprises polymethyl methacrylate resin.

11. The method of claim 7, wherein the step of placing the container in the housing cavity comprises:
  forming a seal with a upper edge of the container in the housing to prevent leakage as the piston applies the pressure against the mixed resin and initiator.

12. The method of claim 7, wherein the cured thermosetting plastic comprises a blank for manufacturing dentures.

13. The method of claim 12, further comprising machining the cured thermosetting plastic by whereby at least a portion of a denture is fabricated.

14. The method of claim 7, further comprising:
  deforming the container;
  forming an impression comprising a groove in a corner of the cured thermosetting plastic.

15. The method of 7, wherein the container comprises a cylindrical container.

16. The method of claim 15, further comprising:
  deforming the container;
  forming an impression comprising an annular groove disposed about the outer circumferential edge of the lower face of the container in response to the deforming, whereby a corresponding impression in the cured thermosetting plastic is formed.

17. A method for molding a thermosetting plastic comprising:
  applying pressure to a container containing a mixed monomer resin and polymerization initiator and comprising an upper edge configured to seal the container from leakage,
  wherein the pressure is applied against the mixed resin and initiator; and
  controlling a curing process of the mixed monomer resin and polymerization initiator into a thermosetting plastic by controlling at least one of: the heat and pressure to minimize at least one of: porosity and shrinkage of the thermosetting plastic;
  deforming the container; and
  forming an impression comprising a groove in a corner of the cured thermosetting plastic in response to the deforming.

* * * * *